(12) United States Patent
Xu et al.

(10) Patent No.: US 10,196,360 B2
(45) Date of Patent: Feb. 5, 2019

(54) CRYSTAL FORMS OF BEDAQUILINE FUMARATE AND PREPARATION METHODS THEREFOR

(71) Applicant: Zhejiang Hisun Pharmaceutical Co., Ltd., Taizhou (CN)

(72) Inventors: Jinyi Xu, Taizhou (CN); Liang Zhang, Taizhou (CN); Xiangyang Zhang, Taizhou (CN); Xinzeng Wang, Taizhou (CN); Jian Chai, Taizhou (CN); Hongying Luo, Taizhou (CN); Zhiqing Yang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/760,090

(22) PCT Filed: Oct. 20, 2015

(86) PCT No.: PCT/CN2015/092343
§ 371 (c)(1),
(2) Date: Mar. 14, 2018

(87) PCT Pub. No.: WO2017/066926
PCT Pub. Date: Apr. 27, 2017

(65) Prior Publication Data
US 2018/0265473 A1    Sep. 20, 2018

(51) Int. Cl.
*C07D 215/227* (2006.01)
*B01D 9/00* (2006.01)
*A61P 31/06* (2006.01)

(52) U.S. Cl.
CPC ....... *C07D 215/227* (2013.01); *B01D 9/0063* (2013.01); *A61P 31/06* (2018.01)

(58) Field of Classification Search
CPC .................................................. C07D 215/227
See application file for complete search history.

(56) References Cited

U.S. PATENT DOCUMENTS

| | | | |
|---|---|---|---|
| 2005/0148581 A1 | 7/2005 | Van Gestel et al. | |
| 2007/0249667 A1 | 10/2007 | Andries et al. | |
| 2010/0028428 A1* | 2/2010 | Hegyi | C07D 215/227 424/474 |

FOREIGN PATENT DOCUMENTS

| | | |
|---|---|---|
| CN | 1671667 A | 9/2005 |
| CN | 1976704 A | 6/2007 |
| CN | 101547904 A | 9/2009 |
| WO | 2008068231 A1 | 6/2008 |
| WO | WO2016058564 * | 4/2016 |

OTHER PUBLICATIONS

International Search Report for PCT/CN2015/092343 dated Jun. 14, 2016.

* cited by examiner

*Primary Examiner* — Rebecca L Anderson
*Assistant Examiner* — Karen Cheng
(74) *Attorney, Agent, or Firm* — Lerner, David, Littenberg, Krumholz & Mentlik, LLP

(57) ABSTRACT

Provided are crystal forms I, II, and III of bedaquiline fumarate, and preparation methods thereof. The crystal forms have high purity, excellent physicochemical properties, and good stability. The preparation methods can effectively improve the quality of products, and are applicable to preparation and mass production of medicines.

4 Claims, 14 Drawing Sheets

CRYSTAL FORMS OF BEDAQUILINE FUMARATE AND PREPARATION METHODS THEREFOR

CROSS REFERENCE TO RELATED APPLICATIONS

The present application is a national phase entry under 35 U.S.C. § 371 of International Application No. PCT/CN2015/092343, filed Oct. 20, 2015, published in Chinese which is hereby incorporated herein by reference.

TECHNICAL FIELD

The present invention relates to the field of pharmacy. More specifically, the present invention relates to new crystal forms of bedaquiline fumarate and the preparation methods thereof.

TECHNICAL BACKGROUND

Bedaquiline fumarate is a new type of anti-tuberculosis drugs, is a biaryl quinoline antibiotics, bactericide for the *Mycobacterium tuberculosis*, the main mechanism of action of bedaquiline fumarate is to inhibit the synthase of adenosine triphosphate (ATP) of *Mycobacterium tuberculosis*, block the energy supply of bacteria. Bedaquiline has the same bactericidal activity against the common and drug resistant (including multidrug-resistant) strains of *Mycobacterium tuberculosis*, is not cross-resistant to existing antituberculosis drugs and is equally effective against dormant bacteria.

The chemical name of bedaquiline fumarate is: (1R,2S)-1-(6-bromo-2-methoxyquinolin-3-yl)-4-dimethylamino-1-phenyl-2-(1-naphthyl)-2-butan of fumarate, the structural formula is:

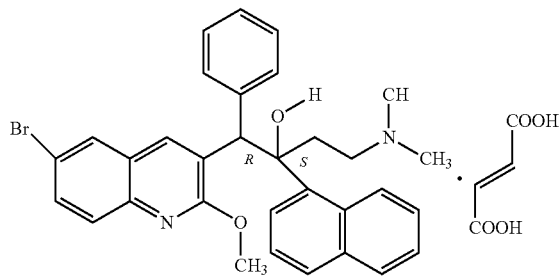

International patent application WO2008/068231 A1 discloses the synthetic method of bedaquiline fumarate.

For polymorphic drugs, different crystal forms may have different physicochemical properties including melting point, chemical stability, apparent solubility, dissolution rate, optical and mechanical properties, which directly affect the quality of the drug substance and the formulation.

SUMMARY OF THE INVENTION

The present invention relates to new crystal forms of bedaquiline fumarate, namely crystal form I, crystal form II and crystal form III.

One of the objects of the present invention is to provide crystal form I of bedaquiline fumarate.

The X-ray powder diffraction pattern of the crystal form I of bedaquiline fumarate provided by the present invention has characteristic peaks at 2θ (°) values of 5.6±0.2, 11.2±0.2, 22.6±0.2, 23.1±0.2, 23.6±0.2, 29.0±0.2.

In one aspect, X-ray powder diffraction pattern of the crystal form I of bedaquiline fumarate provided by the present invention also has characteristic peaks at 2θ (°) values of 3.8±0.2, 16.9±0.2, 18.8±0.2, 19.3±0.2, 20.6±0.2, 20.9±0.2, 21.9±0.2, 26.7±0.2, 28.3±0.2.

Further, the X-ray powder diffraction pattern of the crystal form I of bedaquiline fumarate provided by the present invention has 2θ, d(Å) and relative intensity data as shown in the following Table 1:

TABLE 1

| Peak No. | 2θ (°) | d (Å) | Relative intensity (%) |
|---|---|---|---|
| 1 | 3.8 | 23.1 | 7.4 |
| 2 | 5.6 | 15.5 | 100 |
| 3 | 7.5 | 11.7 | 1.6 |
| 4 | 10.0 | 8.8 | 1.4 |
| 5 | 10.2 | 8.6 | 1.4 |
| 6 | 11.2 | 7.8 | 80.2 |
| 7 | 12.1 | 7.3 | 2.7 |
| 8 | 13.1 | 6.7 | 6.0 |
| 9 | 15.0 | 5.8 | 2.4 |
| 10 | 16.4 | 5.3 | 3.8 |
| 11 | 16.9 | 5.2 | 4.5 |
| 12 | 17.2 | 5.1 | 1.2 |
| 13 | 18.0 | 4.9 | 3.7 |
| 14 | 18.5 | 4.7 | 1.9 |
| 15 | 18.8 | 4.7 | 4.7 |
| 16 | 19.3 | 4.5 | 4.6 |
| 17 | 20.1 | 4.3 | 3.2 |
| 18 | 20.6 | 4.2 | 5.7 |
| 19 | 20.9 | 4.2 | 6.7 |
| 20 | 21.4 | 4.1 | 4.5 |
| 21 | 21.9 | 4.0 | 5.7 |
| 22 | 22.6 | 3.9 | 13.0 |
| 23 | 23.1 | 3.8 | 25.3 |
| 24 | 23.6 | 3.7 | 7.9 |
| 25 | 24.4 | 3.6 | 4.0 |
| 26 | 24.9 | 3.5 | 2.2 |
| 27 | 26.2 | 3.3 | 2.6 |
| 28 | 26.7 | 3.3 | 5.1 |
| 29 | 28.3 | 3.1 | 6.2 |
| 30 | 29.0 | 3.0 | 32.4 |
| 31 | 30.3 | 2.9 | 2.7 |
| 32 | 30.5 | 2.9 | 31.5 |
| 33 | 34.9 | 2.5 | 2.8 |

Unrestrictedly, the crystal form I of bedaquiline fumarate of the present invention has an X-ray powder diffraction pattern as shown in FIG. 1.

The single crystal analytic characteristic of the crystal form I of bedaquiline fumarate is monoclinic, the space group $P2_1$, the unit cell parameters are: a=16.5670 (2), b=10.4873 (1), c=20.1680(2) Å, α=γ=90.0°, β=109.26 (1), unit cell volume V=3308.01(6) Å$^3$, the number of asymmetric units in the unit cell Z=2.

The molecular stereoscopic projection of the crystal form I of bedaquiline fumarate of the present invention is shown in FIG. 2.

The unit cell accumulation projection of the crystal form I of bedaquiline fumarate of the present invention along the b axis is shown in FIG. 3.

In addition, the crystal form I of bedaquiline fumarate of the present invention can be characterized by the infrared absorption spectrum measured by KBr pellet, it has characteristic peaks at about 3408.88 cm$^{-1}$±2 cm$^{-1}$, 2643.66 cm$^{-1}$±2 cm$^{-1}$, 1653.53 cm$^{-1}$±2 cm$^{-1}$, 1314.86 cm$^{-1}$±2 cm$^{-1}$, 1271.71 cm$^{-1}$±2 cm$^{-1}$, 864.48 cm$^{-1}$±2 cm$^{-1}$, 787.56 cm$^{-1}$±2 cm$^{-1}$.

Furthermore, the infrared absorption spectrum of the crystal form I of bedaquiline fumarate has characteristic peaks at about 3408.02 cm$^{-1}$±2 cm$^{-1}$, 3051.07 cm$^{-1}$±2 cm$^{-1}$, 2945.75 cm$^{-1}$±2 cm$^{-1}$, 2895.89 cm$^{-11}$±2 cm$^{-1}$, 2643.66 cm$^{-1}$±2 cm$^{-1}$, 2466.88 cm$^{-1}$±2 cm$^{-1}$, 1701.54 cm$^{-1}$±2 cm$^{-1}$, 1653.53 cm$^{-1}$±2 cm$^{-1}$, 1617.64 cm$^{-1}$±2 cm$^{-1}$, 1597.35 cm$^{-1}$±2 cm$^{-1}$, 1568.56 cm$^{-1}$±2 cm$^{-1}$, 1511.54 cm$^{-1}$±2 cm$^{-1}$, 1489.43 cm$^{-1}$±2 cm$^{-1}$, 1458.54 cm$^{-1}$±2 cm$^{-1}$, 1397.97 cm$^{-1}$±2 cm$^{-1}$, 1344.84 cm$^{-1}$±2 cm$^{-1}$, 1314.86 cm$^{-1}$±2 cm$^{-1}$, 1271.71 cm$^{-1}$±2 cm$^{-1}$, 1249.35 cm$^{-1}$±2 cm$^{-1}$, 1186.53 cm$^{-1}$±2 cm$^{-1}$, 1113.88 cm$^{-1}$±2 cm$^{-1}$, 1086.23 cm$^{-1}$±2 cm$^{-1}$, 1061.46 cm$^{-1}$±2 cm$^{-1}$, 1012.84 cm$^{-1}$±2 cm$^{-1}$, 982.05 cm$^{-1}$±2 cm$^{-1}$, 921.88 cm$^{-1}$±2 cm$^{-1}$, 864.48 cm$^{-1}$±2 cm$^{-1}$, 826.00 cm$^{-1}$±2 cm$^{-1}$, 807.11 cm$^{-1}$±2 cm$^{-1}$, 787.56 cm$^{-1}$±2 cm$^{-1}$, 737.64 cm$^{-1}$±2 cm$^{-1}$, 707.42 cm$^{-1}$±2 cm$^{-1}$, 646.72 cm$^{-1}$±2 cm$^{-1}$, 571.57 cm$^{-1}$±2 cm$^{-1}$, 519.82 cm$^{-1}$±2 cm$^{-1}$, 452.27 cm$^{-1}$±2 cm$^{-1}$.

The infrared spectrum of the crystal form I of bedaquiline fumarate is shown in FIG. 4.

The differential scanning calorimetry (DSC) thermogram of the crystal form I of bedaquiline fumarate of the present invention has a maximum absorption peak within the range of 205-210° C.

The DSC thermogram of the crystal form I of bedaquiline fumarate of the present invention is shown in FIG. 5.

The TGA thermogram of the crystal form I of bedaquiline fumarate of the present invention is shown in FIG. 6.

Another object of the present invention is to provide crystal form II of bedaquiline fumarate.

The X-ray powder diffraction pattern of the crystal form II of bedaquiline fumarate provided by the present invention has characteristic peaks at 2θ (°) values of 4.7±0.2, 7.4±0.2, 9.6±0.2, 16.5±0.2, 16.8±0.2, 18.7±0.2, 19.9±0.2, 21.5±0.2, 21.9±0.2, 24.3±0.2.

In one aspect, X-ray powder diffraction pattern of the crystal form II of bedaquiline fumarate provided by the present invention has characteristic peaks at 2θ (°) values of 3.4±0.2, 8.4±0.2, 11.6±0.2, 12.6±0.2, 14.9±0.2, 20.3±0.2.

Further, the X-ray powder diffraction pattern of the crystal form II of bedaquiline fumarate f the present invention has 2θ, d(Å) and relative intensity data as shown in the following Table 2:

TABLE 2

| Peak No. | 2θ (°) | d (Å) | Relative Intensity (%) |
| --- | --- | --- | --- |
| 1 | 3.4 | 25.5 | 24.6 |
| 2 | 4.7 | 18.5 | 85.8 |
| 3 | 6.6 | 13.2 | 18.7 |
| 4 | 7.4 | 11.8 | 63.8 |
| 5 | 8.4 | 10.4 | 31.2 |
| 6 | 9.6 | 9.1 | 57.5 |
| 7 | 10.4 | 8.4 | 14.8 |
| 8 | 10.8 | 8.1 | 13.6 |
| 9 | 11.6 | 7.5 | 28.8 |
| 10 | 12.2 | 7.2 | 19.6 |
| 11 | 12.6 | 6.9 | 20.7 |
| 12 | 13.0 | 6.7 | 11.0 |
| 13 | 14.1 | 6.2 | 19.7 |
| 14 | 14.9 | 5.9 | 21.6 |
| 15 | 15.7 | 5.6 | 6.4 |
| 16 | 16.5 | 5.3 | 51.9 |
| 17 | 16.8 | 5.2 | 62.2 |
| 18 | 17.7 | 4.9 | 13.9 |
| 19 | 18.7 | 4.7 | 63.1 |
| 20 | 19.9 | 4.4 | 39.1 |
| 21 | 20.3 | 4.3 | 31.5 |
| 22 | 21.5 | 4.1 | 100 |
| 23 | 21.9 | 4.0 | 63.4 |

TABLE 2-continued

| Peak No. | 2θ (°) | d (Å) | Relative Intensity (%) |
| --- | --- | --- | --- |
| 24 | 22.4 | 3.9 | 8.6 |
| 25 | 22.9 | 3.8 | 17.9 |
| 26 | 23.3 | 3.8 | 9.1 |
| 27 | 24.3 | 3.6 | 46.7 |
| 28 | 25.5 | 3.4 | 15.5 |
| 29 | 26.6 | 3.3 | 11.9 |
| 30 | 27.6 | 3.2 | 16.5 |
| 31 | 28.4 | 3.1 | 12.9 |
| 32 | 29.6 | 3.0 | 13.8 |
| 33 | 30.5 | 2.9 | 12.8 |

Unrestrictedly, the crystal form II of bedaquiline fumarate of the present invention has an X-ray powder diffraction pattern as shown in FIG. 7.

In addition, the crystal form II of bedaquiline fumarate of the present invention can be characterized by the infrared absorption spectrum measured by KBr pellet, it has characteristic peaks at about 3408.88 cm$^{-1}$±2 cm$^{-1}$, 2643.66 cm$^{-1}$±2 cm$^{-1}$, 1721.80 cm$^{-1}$±2 cm$^{-1}$, 1314.86 cm$^{-1}$+2 cm$^{-1}$, 865.79 cm$^{-1}$±2 cm$^{-1}$, 776.91 cm$^{-1}$±2 cm$^{-1}$.

It has characteristic peaks at about 3407.87 cm$^{-1}$±2 cm$^{-1}$, 3053.08 cm$^{-1}$±2 cm$^{-1}$, 2947.27 cm$^{-1}$±2 cm$^{-1}$, 2643.00 cm$^{-1}$±2 cm$^{-1}$, 2468.67 cm$^{-1}$±2 cm$^{-1}$, 1721.80 cm$^{-1}$±2 cm$^{-1}$, 1614.74 cm$^{-1}$±2 cm$^{-1}$, 1598.51 cm$^{-1}$±2 cm$^{-1}$, 1568.58 cm$^{-1}$±2 cm$^{-1}$, 1511.95 cm$^{-1}$±2 cm$^{-1}$, 1489.71 cm$^{-1}$±2 cm$^{-1}$, 1458.97 cm$^{-1}$±2 cm$^{-1}$, 1398.40 cm$^{-1}$±2 cm$^{-1}$, 1344.64 cm$^{-1}$±2 cm$^{-1}$, 1271.64 cm$^{-1}$±2 cm$^{-1}$, 1250.44 cm$^{-1}$±2 cm$^{-1}$, 1179.60 cm$^{-1}$±2 cm$^{-1}$, 1112.91 cm$^{-1}$±2 cm$^{-1}$, 1084.60 cm$^{-1}$±2 cm$^{-1}$, 1062.20 cm$^{-1}$+2 cm$^{-1}$, 1012.81 cm$^{-1}$±2 cm$^{-1}$, 981.29 cm$^{-1}$±2 cm$^{-1}$, 922.75 cm$^{-1}$±2 cm$^{-1}$, 865.79 cm$^{-1}$±2 cm$^{-1}$, 825.16 cm$^{-1}$±2 cm$^{-1}$, 806.17 cm$^{-1}$±2 cm$^{-1}$, 776.91 cm$^{-1}$±2 cm$^{-1}$, 738.42 cm$^{-1}$±2 cm$^{-1}$, 709.51 cm 1±2 cm$^{-1}$, 646.09 cm$^{-1}$±2 cm$^{-1}$, 570.10 cm$^{-1}$±2 cm$^{-1}$, 520.71 cm$^{-1}$±2 cm$^{-1}$, 477.72 cm$^{-1}$±2 cm$^{-1}$, 451.76 cm$^{-1}$±2 cm$^{-1}$.

The infrared spectrum of the crystal form II of bedaquiline fumarate is shown in FIG. 8.

The differential scanning calorimetry (DSC) thermogram of the crystal form II of bedaquiline fumarate of the present invention has a maximum absorption peak within the range of 205-210° C.

The DSC thermogram of the crystal form II of bedaquiline fumarate of the present invention is shown in FIG. 9.

The TGA thermogram of the crystal form II of bedaquiline fumarate of the present invention is shown in FIG. 10.

Another object of the present invention is to provide crystal form III of bedaquiline fumarate.

The X-ray powder diffraction pattern of the crystal form III of bedaquiline fumarate provided by the present invention has characteristic peaks at 2θ (°) values of 6.1±0.2, 10.4±0.2, 12.0±0.2, 14.1±0.2, 16.9±0.2, 18.9±0.2, 20.5±0.2, 20.8±0.2, 21.5±0.2, 23.2±0.2.

In one aspect, X-ray powder diffraction pattern of the crystal form III of bedaquiline fumarate provided by the present invention has characteristic peaks at 2θ (°) values of 13.2±0.2, 19.3±0.2, 20.0±0.2, 24.9±0.2, 26.9±0.2, 27.3±0.2.

Further, the X-ray powder diffraction pattern of the crystal form III of bedaquiline fumarate of the present invention has 2θ, d(Å) and relative intensity data as shown in the following Table 3:

TABLE 3

| Peak No. | 2θ (°) | d (Å) | Relative Intensity (%) |
|---|---|---|---|
| 1 | 6.1 | 14.4 | 19.9 |
| 2 | 10.4 | 8.4 | 22.4 |
| 3 | 12.0 | 7.3 | 25.9 |
| 4 | 12.6 | 6.9 | 5.5 |
| 5 | 13.2 | 6.6 | 14.7 |
| 6 | 14.1 | 6.2 | 42.8 |
| 7 | 14.8 | 5.9 | 8.4 |
| 8 | 15.6 | 5.6 | 2.6 |
| 9 | 16.9 | 5.2 | 31.5 |
| 10 | 18.1 | 4.8 | 11.6 |
| 11 | 18.9 | 4.6 | 20.6 |
| 12 | 19.3 | 4.5 | 13.1 |
| 13 | 20.0 | 4.4 | 13.1 |
| 14 | 20.5 | 4.3 | 42.0 |
| 15 | 20.8 | 4.2 | 21.8 |
| 16 | 21.5 | 4.1 | 33.2 |
| 17 | 23.2 | 3.8 | 100.0 |
| 18 | 23.9 | 3.7 | 10.1 |
| 19 | 24.2 | 3.6 | 4.6 |
| 20 | 24.9 | 3.5 | 13.0 |
| 21 | 25.6 | 3.4 | 11.0 |
| 22 | 26.2 | 3.3 | 4.7 |
| 23 | 26.9 | 3.3 | 12.0 |
| 24 | 27.3 | 3.2 | 12.1 |
| 25 | 28.0 | 3.1 | 7.4 |
| 26 | 28.7 | 3.1 | 6.6 |
| 27 | 29.7 | 3.0 | 8.3 |
| 28 | 30.6 | 2.9 | 3.1 |
| 29 | 31.1 | 2.8 | 3.0 |
| 30 | 31.6 | 2.8 | 3.7 |
| 31 | 32.4 | 2.7 | 4.1 |
| 32 | 34.4 | 2.6 | 6.6 |
| 33 | 36.6 | 2.4 | 4.9 |

Unrestrictedly, the crystal form III of bedaquiline fumarate of the present invention has an X-ray powder diffraction pattern as shown in FIG. 11.

In addition, the crystal form III of bedaquiline fumarate of the present invention can be characterized by the infrared absorption spectrum measured by KBr pellet, it has characteristic peaks at about 1700.95 cm$^{-1}$±2 cm$^{-1}$, 1636.91 cm$^{-1}$±2 cm$^{-1}$, 1597.23 cm$^{-1}$±2 cm$^{-1}$, 1563.58 cm$^{-1}$+2 cm$^{-1}$, 1490.53 cm$^{-1}$±2 cm$^{-1}$, 1459.10 cm$^{-1}$±2 cm$^{-1}$, 1392.58 cm$^{-1}$±2 cm$^{-1}$, 1342.09 cm$^{-1}$±2 cm$^{-1}$, 1251.42 cm$^{-1}$±2 cm$^{-1}$, 1168.11 cm$^{-1}$±2 cm$^{-1}$, 1059.74 cm$^{-1}$±2 cm$^{-1}$, 922.20 cm$^{-1}$±2 cm$^{-1}$.

It has characteristic peaks at about 3254.22 cm$^{-1}$±2 cm$^{-1}$, 3053.33 cm$^{-1}$±2 cm$^{-1}$, 3018.53 cm$^{-1}$±2 cm$^{-1}$, 2950.40 cm$^{-1}$±2 cm$^{-1}$, 2780.20 cm$^{-1}$±2 cm$^{-1}$, 2586.97 cm$^{-1}$±2 cm$^{-1}$, 2465.99 cm$^{-1}$±2 cm$^{-1}$, 1700.95 cm$^{-1}$±2 cm$^{-1}$, 1636.91 cm$^{-1}$±2 cm$^{-1}$, 1618.28 cm$^{-1}$±2 cm$^{-1}$, 1597.23 cm$^{-1}$±2 cm-1, 1563.58 cm$^{-1}$±2 cm$^{-1}$, 1512.77 cm$^{-1}$±2 cm$^{-1}$, 1490.53 cm$^{-1}$±2 cm$^{-1}$, 1459.10 cm$^{-1}$±2 cm$^{-1}$, 1392.58 cm$^{-1}$±2 cm$^{-1}$, 1342.09 cm$^{-1}$±2 cm$^{-1}$, 1283.13 cm$^{-1}$±2 cm$^{-1}$, 1251.42 cm$^{-1}$±2 cm$^{-1}$, 1210.13 cm$^{-1}$±2 cm$^{-1}$, 1190.04 cm$^{-1}$±2 cm$^{-1}$, 1168.11 cm$^{-1}$±2 cm$^{-1}$, 1113.52 cm$^{-1}$±2 cm$^{-1}$, 1084.19 cm$^{-1}$±2 cm$^{-1}$, 1059.74 cm$^{-1}$±2 cm$^{-1}$, 985.01 cm$^{-1}$±2 cm$^{-1}$, 922.20 cm$^{-1}$±2 cm$^{-1}$, 893.07 cm$^{-1}$±2 cm$^{-1}$, 830.44 cm$^{-1}$±2 cm$^{-1}$, 801.78 cm$^{-1}$±2 cm$^{-1}$, 777.37 cm$^{-1}$±2 cm$^{-1}$, 734.79 cm$^{-1}$±2 cm$^{-1}$, 712.87 cm$^{-1}$±2 cm$^{-1}$, 698.76 cm$^{-1}$±2 cm$^{-1}$, 640.44 cm$^{-1}$±2 cm$^{-1}$, 571.91 cm$^{-1}$±2 cm$^{-1}$, 543.33 cm$^{-1}$±2 cm$^{-1}$, 520.93 cm 1±2 cm$^{-1}$, 486.22 cm$^{-1}$±2 cm$^{-1}$, 458.91 cm$^{-1}$±2 cm$^{-1}$, 427.64 cm$^{-1}$±2 cm$^{-1}$.

The infrared spectrum of the crystal form III of bedaquiline fumarate is shown in FIG. 12.

The differential scanning calorimetry (DSC) thermogram of the crystal form III of bedaquiline fumarate of the present invention has a maximum absorption peak within the range of 205-207° C.

The DSC thermogram of the crystal form III of bedaquiline fumarate of the present invention is shown in FIG. 13.

The TGA thermogram of the crystal form III of bedaquiline fumarate of the present invention is shown in FIG. 14.

Another object of the present invention is to provide a method for preparing crystal form I of bedaquiline fumarate comprising the following steps:

(1)(1R,2S)-1-(6-bromo-2-methoxyquinolin-3-yl)-4-dimethylamino-1-phenyl-2-(1-naphthyl)-2-butanol fumarate is dissolved in a mixed solvent of methanol and water;

(2) the temperature is increased to 50-60° C. and the solution is stirred continuously until the solute dissolved;

(3) filtered, the filtrate is stirred to decrease the temperature to 10-25° C.; and (4) crystallized at 10-25° C., filtered to obtain the crystal form I of (1R,2S)-1-(6-bromo-2-methoxyquinolin-3-yl)-4-dimethylamino-1-phenyl-2-(1-naphthyl)-2-butanol fumarate.

In one aspect, the weight-to-volume ratio of bedaquiline fumarate to the mixed solvent of methanol and water is 1:10-50 g/ml, preferably 1:10-20 g/ml; the volume percentage of water is preferably 10%-70%, more preferably 20%-40%.

Another object of the present invention is to provide a method for preparing crystal form II of bedaquiline fumarate comprising the following steps:

(1)(1R,2S)-1-(6-bromo-2-methoxyquinolin-3-yl)-4-dimethylamino-1-phenyl-2-(1-naphthyl)-2-butanol fumarate is dissolved in a mixed solvent of methanol and ethyl acetate or a mixed solvent of methanol and ethanol;

(2) the temperature is increased to 50-60° C. and the solution is stirred continuously until the solute dissolved;

(3) filtered, the filtrate is stirred to decrease the temperature to 10-25° C.; and (4) crystallized at 10-25° C., filtered to obtain the crystal form II of (1R,2S)-1-(6-bromo-2-methoxyquinolin-3-yl)-4-dimethylamino-1-phenyl-2-(1-naphthyl)-2-butanol fumarate.

In one aspect, the weight-to-volume ratio of bedaquiline fumarate to the mixed solvent of methanol and ethyl acetate is 1:1-20 g/ml, preferably 1:5-10 g/ml; the volume percentage of methanol in the mixed solvent is 40%-99%, preferably 50%-70%.

In one aspect, the weight-to-volume ratio of bedaquiline fumarate to the mixed solvent of methanol and ethanol is 1:1-20 g/ml, preferably 1:5-15 g/ml; the volume percentage of methanol in the mixed solvent is 40%-80%, preferably 50%-60%.

A further object of the present invention is to provide a method for preparing crystal form III of bedaquiline fumarate comprising the following steps:

(1) (1R,2S)-1-(6-bromo-2-methoxyquinolin-3-yl)-4-dimethylamino-1-phenyl-2-(1-naphthyl)-2-butanol fumarate is dissolved in isopropanol;

(2) the temperature is increased to about 60-80° C. and the solution is stirred continuously until the solute dissolved;

(3) filtered, the filtrate is stirred to decrease the temperature to 0-5° C.; and (4) crystallized at 0-5° C., filtered to obtain the crystal form III of (1R,2S)-1-(6-bromo-2-methoxyquinolin-3-yl)-4-dimethylamino-1-phenyl-2-(1-naphthyl)-2-butanol fumarate.

The X-ray powder diffractometer (XRPD) and the test conditions involved in the present invention are: X-ray powder diffractometer model Rigaku D/max-2200 Cu target; operation method: scanning speed 4°/min, scanning step width 0.01°.

The single-crystal diffractometer and the test conditions involved in the present invention are: diffraction intensity data collected by Bruker SMART APEX-II diffractometer, CuK$_\alpha$ radiation, graphite monochromator, the diameter of the single tube Φ=0.50 mm, the distance between the crystal and CCD detector d=60.3 mm, tube pressure 40 kV, tube current 30 mA, scanning method: φ/ω scanning The infrared spectrophotometer and the test conditions involved in the present invention are: infrared spectrophotometer model: BRWKER VECTOR 22; operation method: using KBr pellet method, scanning range 400-4000 cm$^{-1}$.

The test conditions for DSC involved in the present invention are: differential scanning calorimeter model: NETZSCH DSC200 F3 Maia; operation method: heating rate 10° C./min, temperature range: 30° C.-250° C.

The test conditions for TGA involved in the present invention are: thermogravimetric analyzer model: PerkinElmer TGA400; operation method: heating rate 10° C./min, temperature range: 30° C.-300° C.

The test conditions for the particle size involved in the present invention are: Mastersizer model: Mastersizer 2000; operation method: 20 mg of bedaquiline fumarate sample is taken, about 5.0 ml dispersant (n-hexane) is added, the sample is subjected to ultrasonication for 1.0 min, is allowed to stabilize for 0.5-1.0 min and then is tested.

The test conditions for liquid chromatography involved in the present invention are: chromatographic column: Ultimate AQ C18, 250×4.6 mm, 5 μm; mobile phase A: acetonitrile and 0.1% trifluoroacetic acid, mobile phase B: water and 0.1% trifluoroacetic acid; detection wavelength: 220 nm; flow rate: 1 ml/min; injection volume: 10 μl.

The conditions for liquid chromatography are shown in the following Table 4:

TABLE 4

| t (min) | A (%) | B (%) |
| --- | --- | --- |
| 0 | 10 | 90 |
| 5 | 10 | 90 |
| 15 | 50 | 50 |
| 25 | 90 | 10 |
| 35 | 90 | 10 |
| 36 | 10 | 90 |
| 40 | 10 | 90 |

After extensive research, the inventors of the present invention found that the new crystal forms of bedaquiline fumarate successfully improve the deficiencies of the prior art, and the drugs comprising the crystal forms of the present invention have the advantages of high purities and excellent physical and chemical properties, good stability, the crystallization methods thereof can effectively improve product quality and can be effectively used in the preparation of drugs and large-scale production and so on.

EMBODIMENTS

Figure 1:
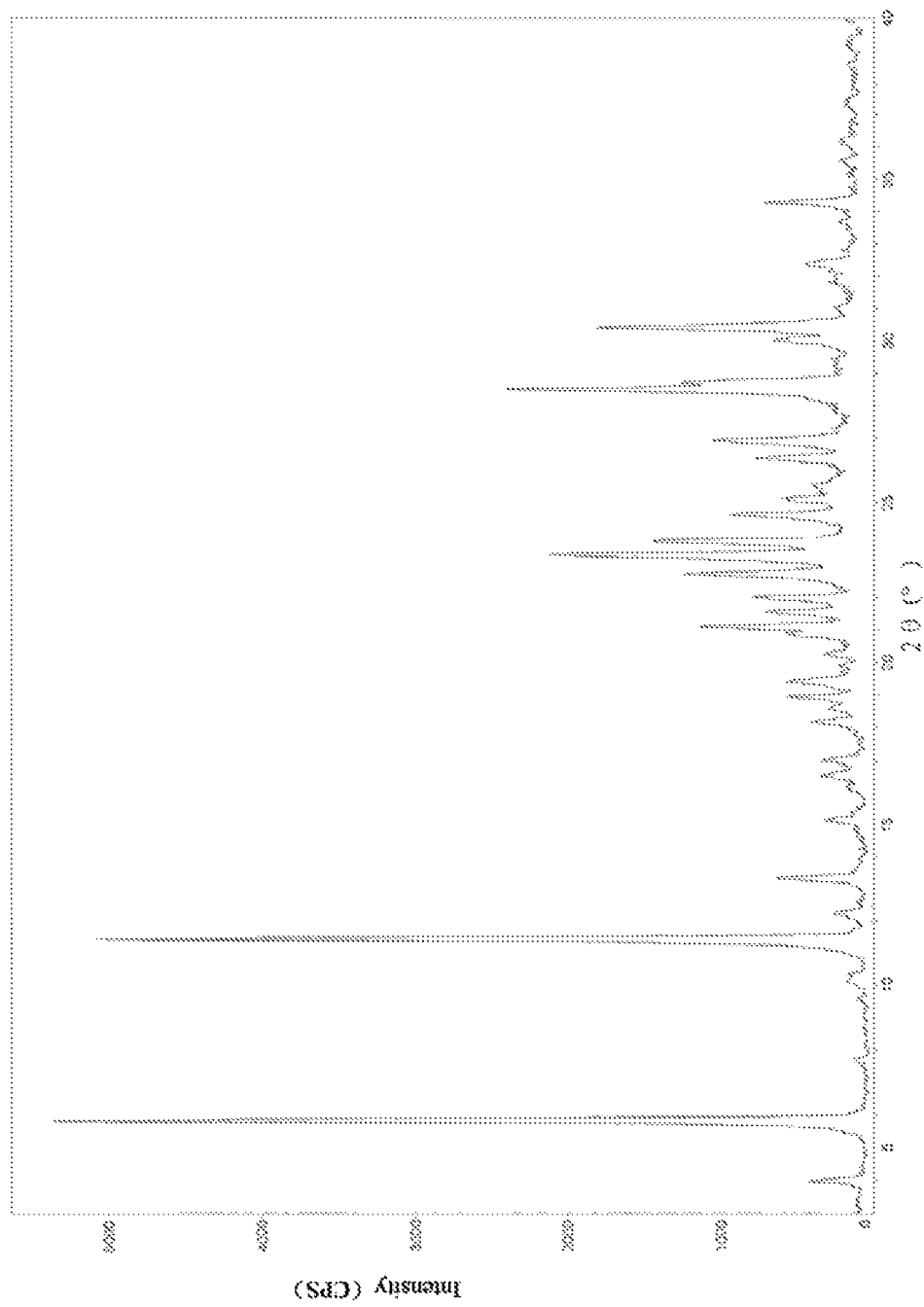
FIG. 1 is an X-ray powder diffraction pattern of crystal form I of bedaquiline fumarate obtained in Example 1.
Figure 2:
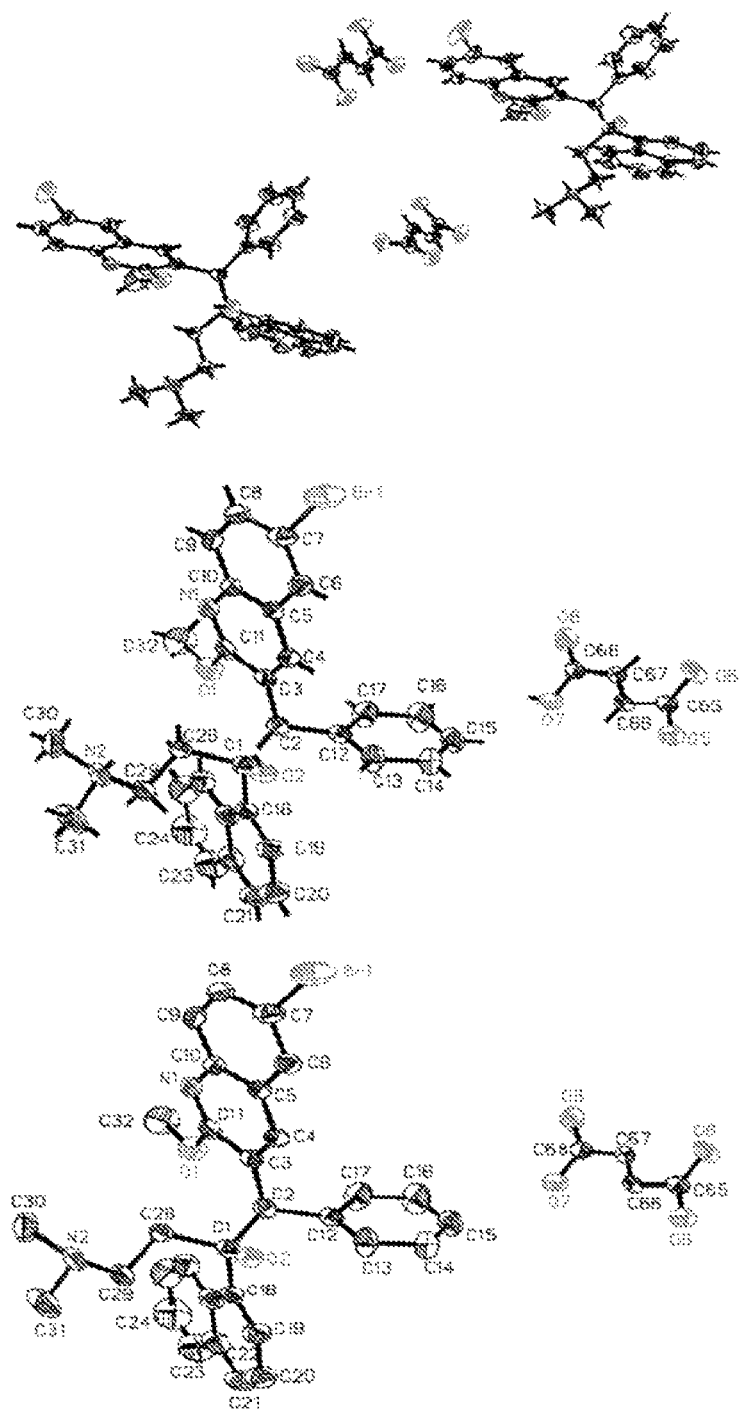
FIG. 2 is molecular stereoscopic projection of crystal form I of bedaquiline fumarate obtained in Example 1.
Figure 3:
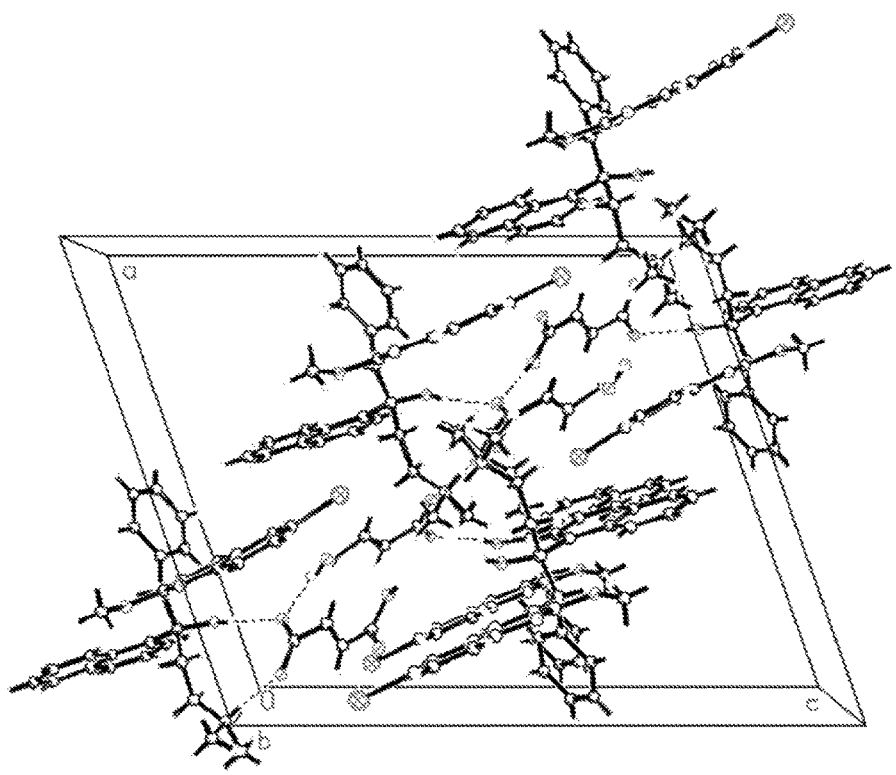
FIG. 3 is the unit cell accumulation projection of crystal form I of bedaquiline fumarate obtained in Example 1 along the b axis.

The following examples further illustrate the present invention, however, they do not constitute a limitation on the present invention.

Preparation of Crude Bedaquiline Fumarate:

Bedaquiline free base (1.19 g), fumaric acid (0.25 g), isopropanol (21 ml) were added into a 100 ml single-necked flask, heated to 70-80° C. until the solution is clear, stirred with heat-preservation for 1 h. Solids were precipitated when the solution was cooled to 50-70° C., the temperature was decreased to 5° C. and the solution was stirred for 1 h, filtered, the filter cake was washed with 10 ml isopropanol, dried at 60° C., −0.1 MPa to obtain end-product bedaquiline fumarate (1.20 g, yield=84%), and it is used as crude material for each example.

Example 1

1 g of bedaquiline fumarate crude product (HPLC purity >99%) was dissolved in 10 ml of mixed solution of methanol and water (methanol:water=4:1), the solution was heated up to 50° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.50 g of crystals, HPLC=99.7%.

Figure 4:
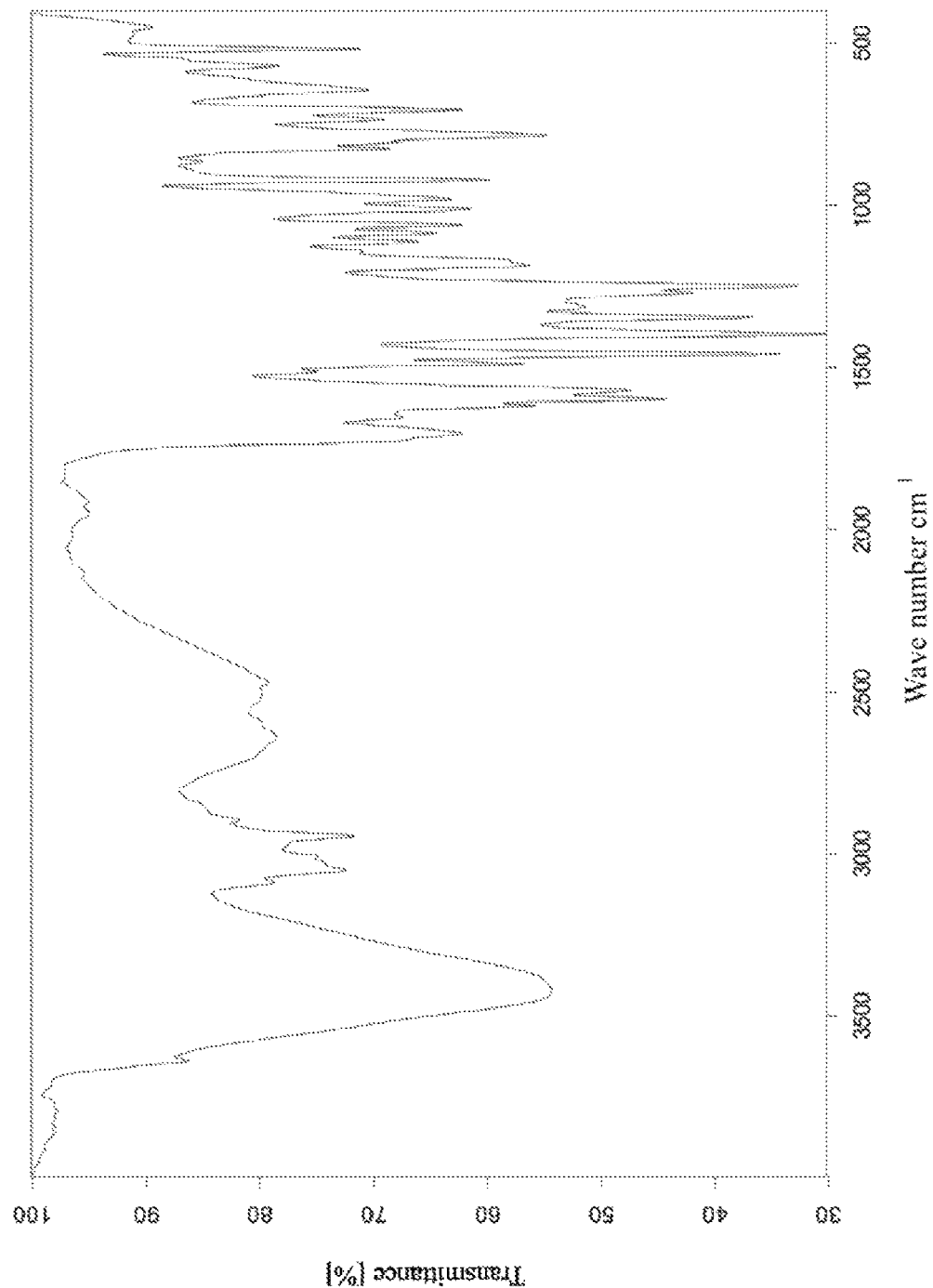
FIG. 4 is an infrared absorption spectrum of crystal form I of bedaquiline fumarate obtained in Example 1.
Figure 5:
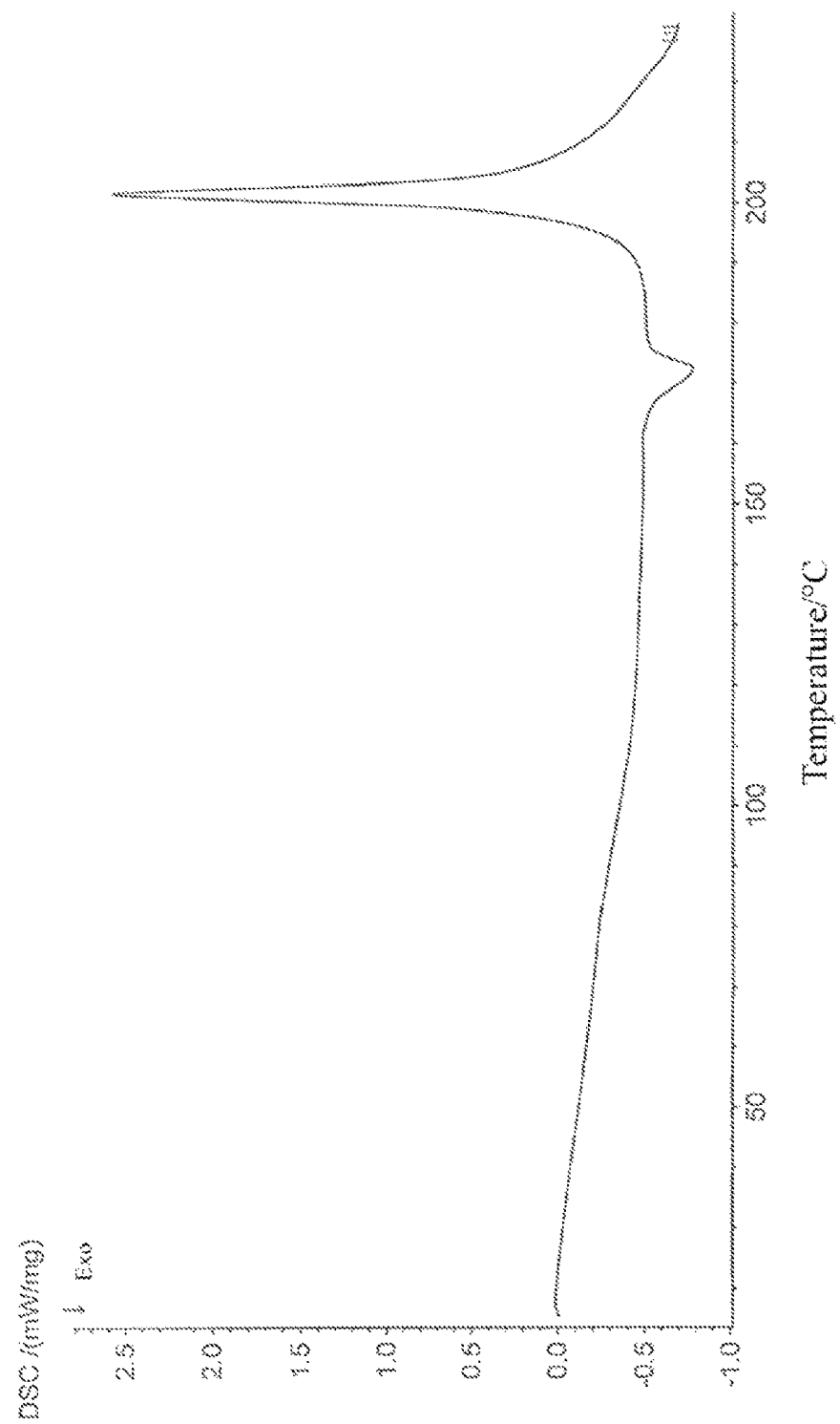
FIG. 5 is a DSC thermogram of crystal form I of bedaquiline fumarate obtained in Example 1.
Figure 6:
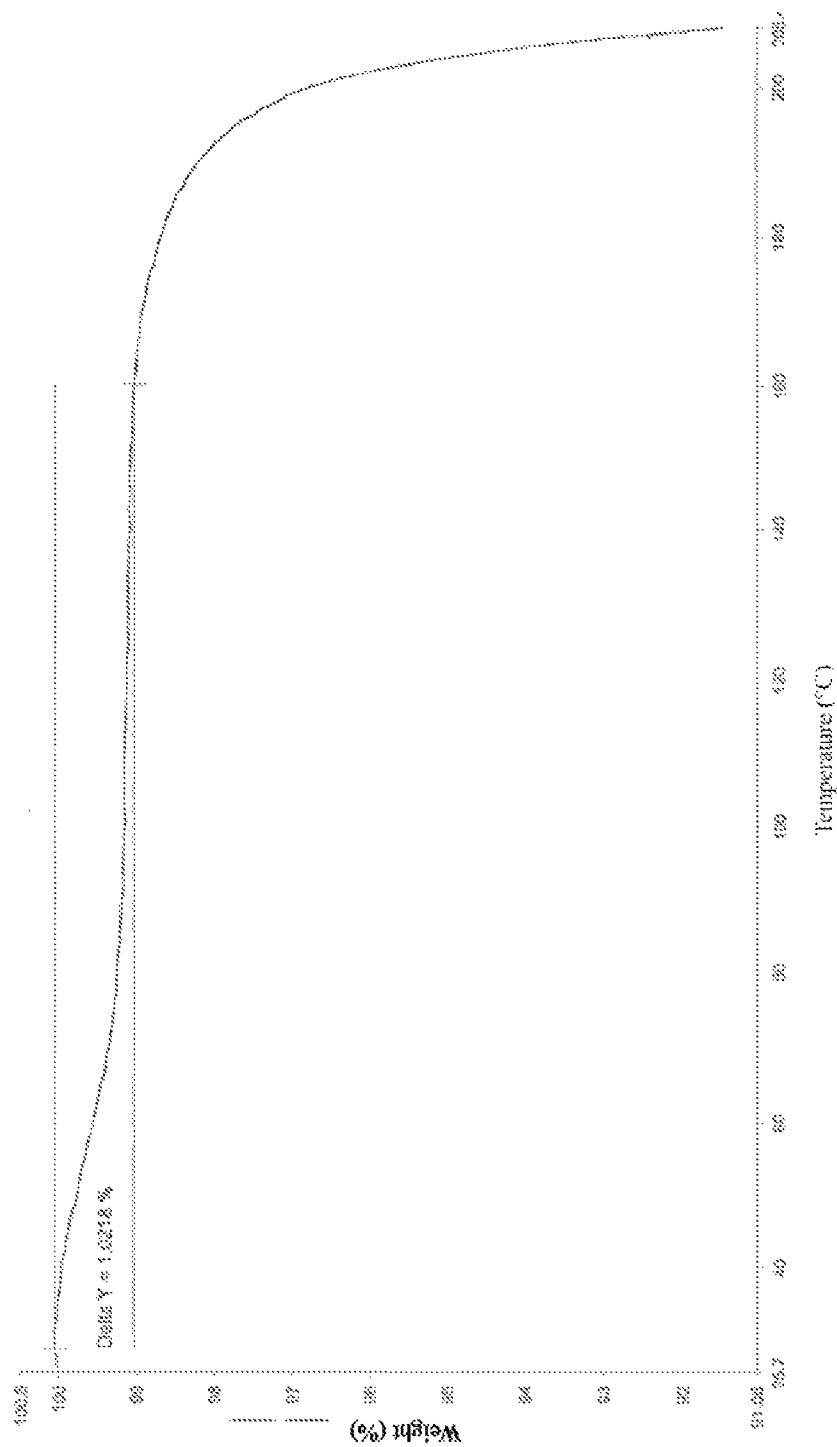
FIG. 6 is a TGA thermogram of crystal form I of bedaquiline fumarate obtained in Example 1.

X-ray powder diffraction, infrared, DSC, and TGA measurements confirmed that the product was the crystal form I of bedaquiline fumarate, the X-ray powder diffraction pattern, infrared absorption spectrum, DSC thermogram and TGA thermogram are shown in FIGS. 1, 4, 5 and 6, respectively.

Example 2

1 g of bedaquiline fumarate crude product (HPLC purity >99%) was dissolved in 10 ml of mixed solution of methanol and water (methanol:water=3:2), the solution was heated up to 60° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.65 g of crystals, HPLC=99.5%.

X-ray powder diffraction, infrared, DSC, and TGA measurements confirmed that the product was the crystal form I of bedaquiline fumarate.

Example 3

1 g of bedaquiline fumarate crude product (HPLC purity >99%) was dissolved in 20 ml of mixed solution of methanol and water (methanol:water=4:1), the solution was heated up to 50° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.3 g of crystals, HPLC=99.7%.

X-ray powder diffraction, infrared, DSC, and TGA measurements confirmed that the product was the crystal form I of bedaquiline fumarate.

Example 4

1 g of bedaquiline fumarate crude product (HPLC purity >99%) was dissolved in 20 ml of mixed solution of methanol and water (methanol:water=3:2), the solution was heated up to 60° C. and was stirred continuously for 30 min to dissolve; filtered, the stirring rate was controlled at 200 rpm/min, the filtrate was cooled to 15° C. at a rate of 6° C./h, and was crystallized under stirring at 15° C. for 4 h, filtered, dried under vacuum at 40° C. to give 0.27 g of crystals, HPLC=99.6%.

X-ray powder diffraction, infrared, DSC, and TGA measurements confirmed that the product was the crystal form I of bedaquiline fumarate.

Example 5

1 g of bedaquiline fumarate crude product (HPLC purity >99%) was dissolved in 15 ml of mixed solution of methanol and water (methanol:water=7:3), the solution was heated up to 60° C. and was stirred continuously for 30 min to dissolve; filtered, the stirring rate was controlled at 200 rpm/min, the filtrate was cooled to 10° C. at a rate of 6° C./h, and was crystallized under stirring at 10° C. for 4 h, filtered, dried under vacuum at 40° C. to give 0.34 g of crystals, HPLC=99.6%.

X-ray powder diffraction, infrared, DSC, and TGA measurements confirmed that the product was the crystal form I of bedaquiline fumarate.

Example 6

1 g of bedaquiline fumarate crude product (HPLC purity >99%) was dissolved in 5 ml of mixed solution of methanol and ethyl acetate (methanol:ethyl acetate=7:3), the solution was heated up to 60° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.6 g of crystals, HPLC=99.7%.

Figure 7:
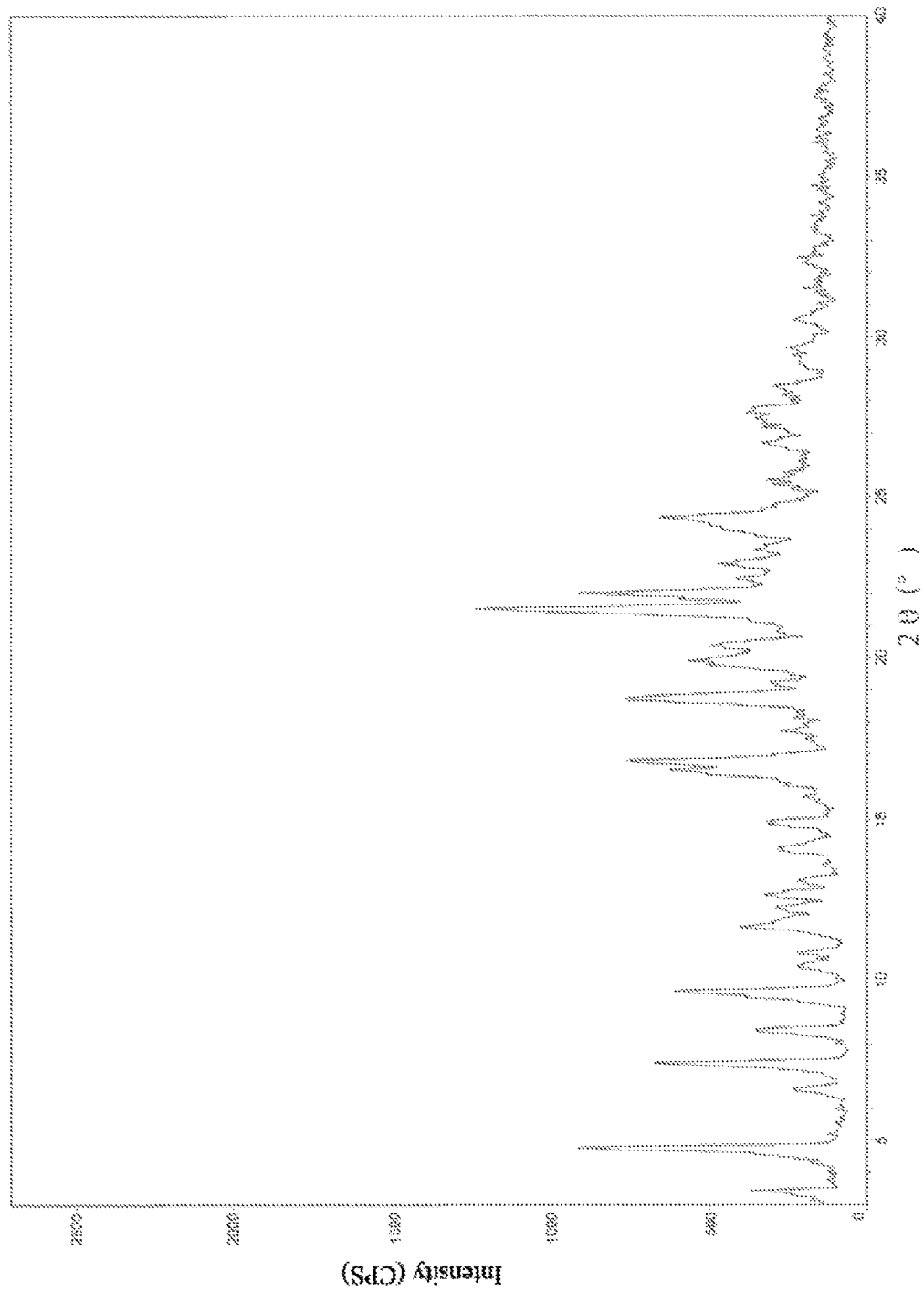
FIG. 7 is an X-ray powder diffraction pattern of crystal form II of bedaquiline fumarate obtained in Example 6.
Figure 8:
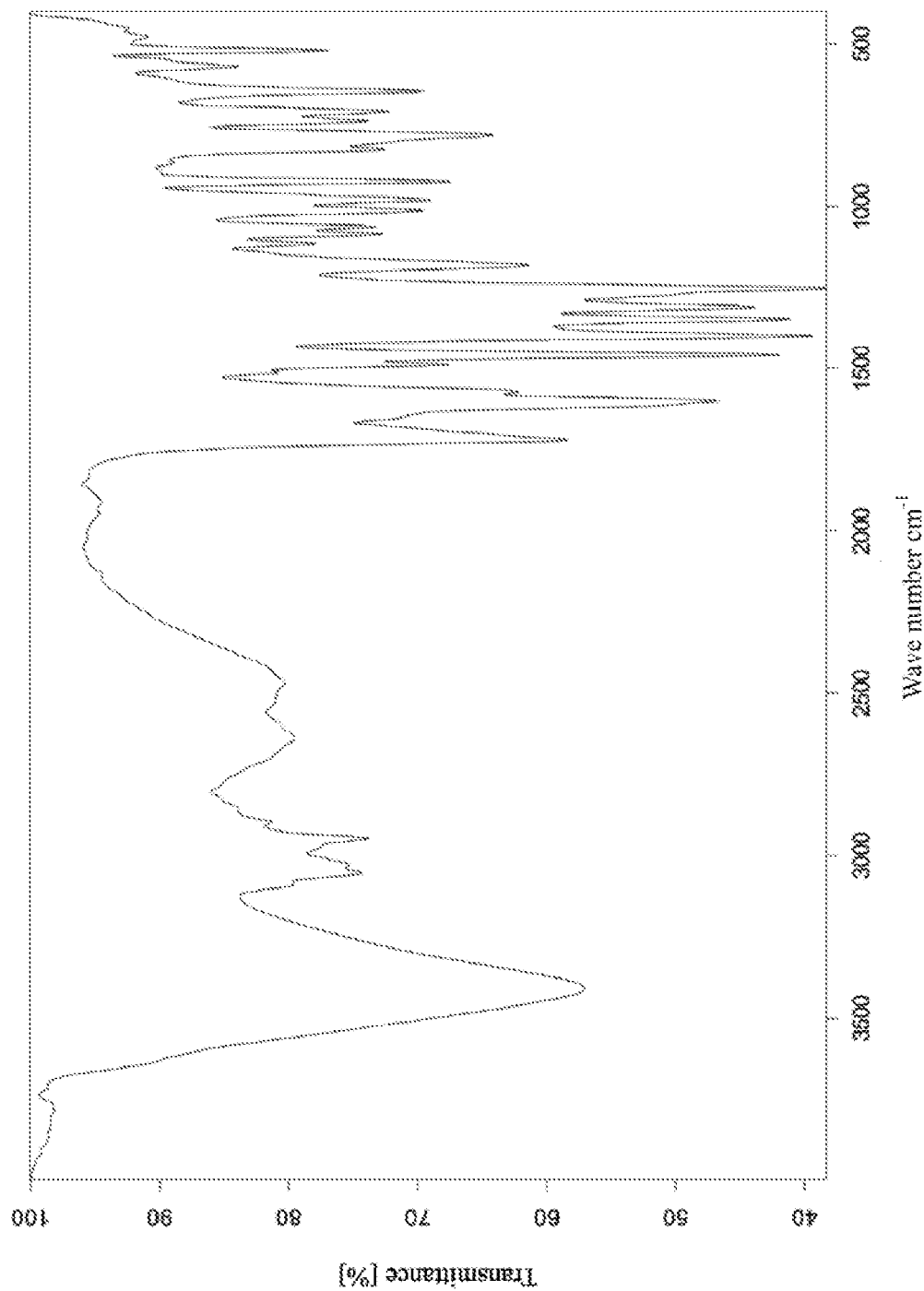
FIG. 8 is an infrared absorption spectrum of crystal form II of bedaquiline fumarate obtained in Example 6.
Figure 9:
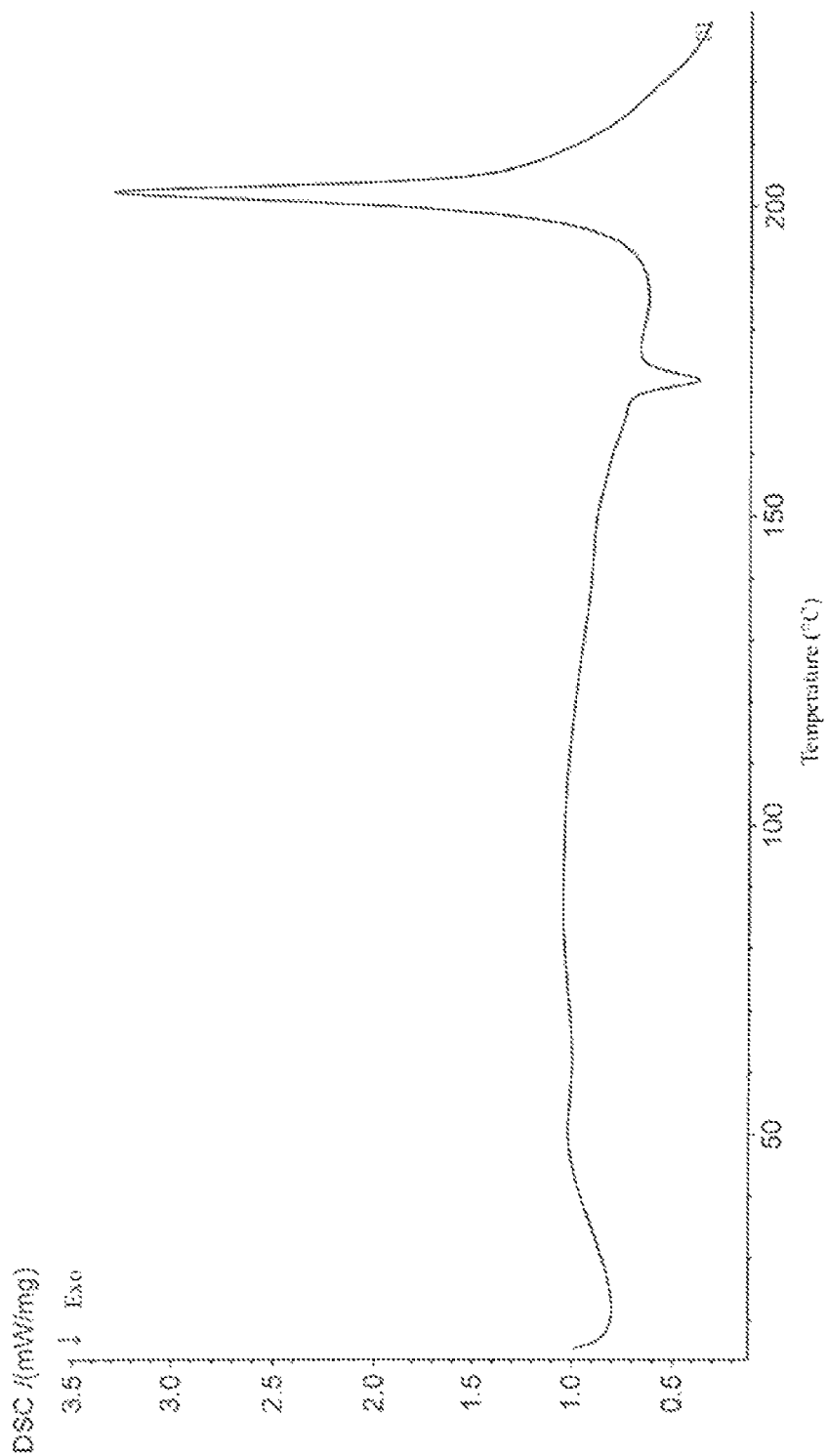
FIG. 9 is a DSC thermogram of crystal form II of bedaquiline fumarate obtained in Example 6.
Figure 10:
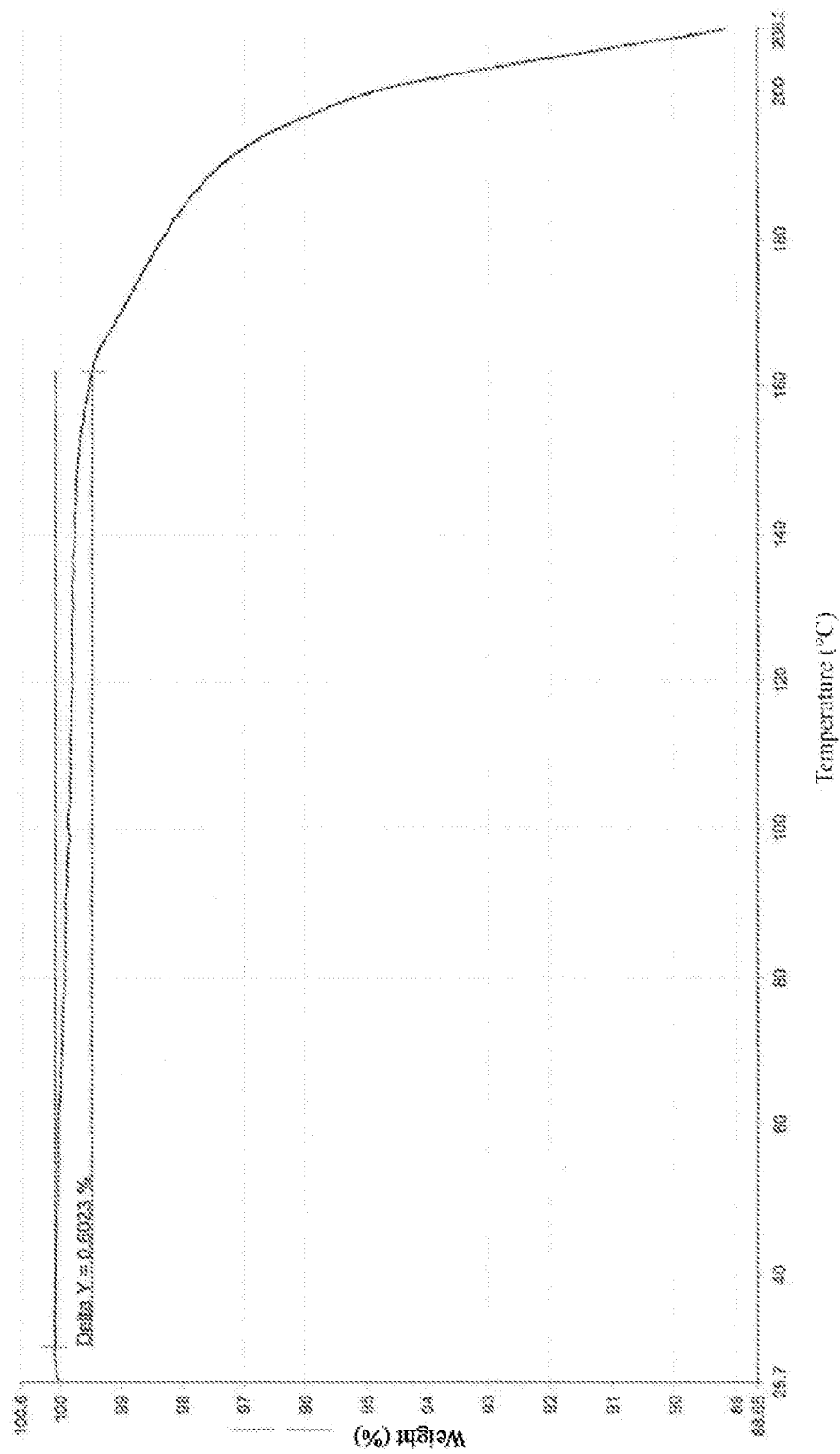
FIG. 10 is a TGA thermogram of crystal form II of bedaquiline fumarate obtained in Example 6.

X-ray powder diffraction, infrared, DSC, and TGA measurements confirmed that the product was the crystal form II of bedaquiline fumarate, the X-ray powder diffraction pattern, infrared absorption spectrum, DSC thermogram and TGA thermogram are shown in FIGS. 7-10, respectively.

Example 7

1 g of bedaquiline fumarate crude product (HPLC purity >99%) was dissolved in 10 ml of mixed solution of methanol and ethyl acetate (methanol:ethyl acetate=6:4), the solution was heated up to 50° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.32 g of crystals, HPLC=99.6%.

X-ray powder diffraction, infrared, DSC, and TGA measurements confirmed that the product was the crystal form II of bedaquiline fumarate.

Example 8

1 g of bedaquiline fumarate crude product (HPLC purity >99%) was dissolved in 8 ml of mixed solution of methanol and ethyl acetate (methanol:ethyl acetate=1:1), the solution was heated up to 50° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.53 g of crystals, HPLC=99.6%.

X-ray powder diffraction, infrared, DSC, and TGA measurements confirmed that the product was the crystal form II of bedaquiline fumarate.

Example 9

1 g of bedaquiline fumarate crude product (HPLC purity >99%) was dissolved in 15 ml of mixed solution of methanol and ethanol (methanol:ethanol=1:1), the solution was heated up to 60° C. and was stirred continuously for 30 min to dissolve; filtered, the stirring rate was controlled at 200 rpm/min, the filtrate was cooled to 25° C. at a rate of 6° C./h, and was crystallized under stirring at 25° C. for 4 h, filtered, dried under vacuum at 40° C. to give 0.6 g of crystals, HPLC=99.6%.

X-ray powder diffraction, infrared, DSC, and TGA measurements confirmed that the product was the crystal form II of bedaquiline fumarate.

Example 10

1 g of bedaquiline fumarate crude product (HPLC purity >99%) was dissolved in 5 ml of mixed solution of methanol and ethanol (methanol:ethanol=7:3), the solution was heated up to 60° C. and was stirred continuously for 30 min to dissolve; filtered, the stirring rate was controlled at 200 rpm/min, the filtrate was cooled to 15° C. at a rate of 6° C./h, and was crystallized under stirring at 15° C. for 4 h, filtered, dried under vacuum at 40° C. to give 0.61 g of crystals, HPLC=99.5%.

X-ray powder diffraction, infrared, DSC, and TGA measurements confirmed that the product was the crystal form II of bedaquiline fumarate.

Example 11

1 g of bedaquiline fumarate crude product (HPLC purity >99%) was dissolved in 10 ml of mixed solution of methanol and ethanol (methanol:ethanol=6:4), the solution was heated up to 60° C. and was stirred continuously for 30 min to dissolve; filtered, the stirring rate was controlled at 200 rpm/min, the filtrate was cooled to 10° C. at a rate of 6° C./h, and was crystallized under stirring at 10° C. for 4 h, filtered, dried under vacuum at 40° C. to give 0.45 g of crystals, HPLC=99.5%.

X-ray powder diffraction, infrared, DSC, and TGA measurements confirmed that the product was the crystal form II of bedaquiline fumarate.

Example 12

1 g of bedaquiline fumarate crude product (HPLC purity >99%) was dissolved in 70 ml of isopropanol, the solution was heated up to 70° C. and was stirred continuously for 30 min to dissolve; filtered, the stirring rate was controlled at 200 rpm/min, the filtrate was cooled to 5° C. at a rate of 6° C./h, and was crystallized under stirring at 5° C. for 4 h, filtered, dried under vacuum at 40° C. to give 0.21 g of crystals, HPLC=99.6%.

Figure 11:
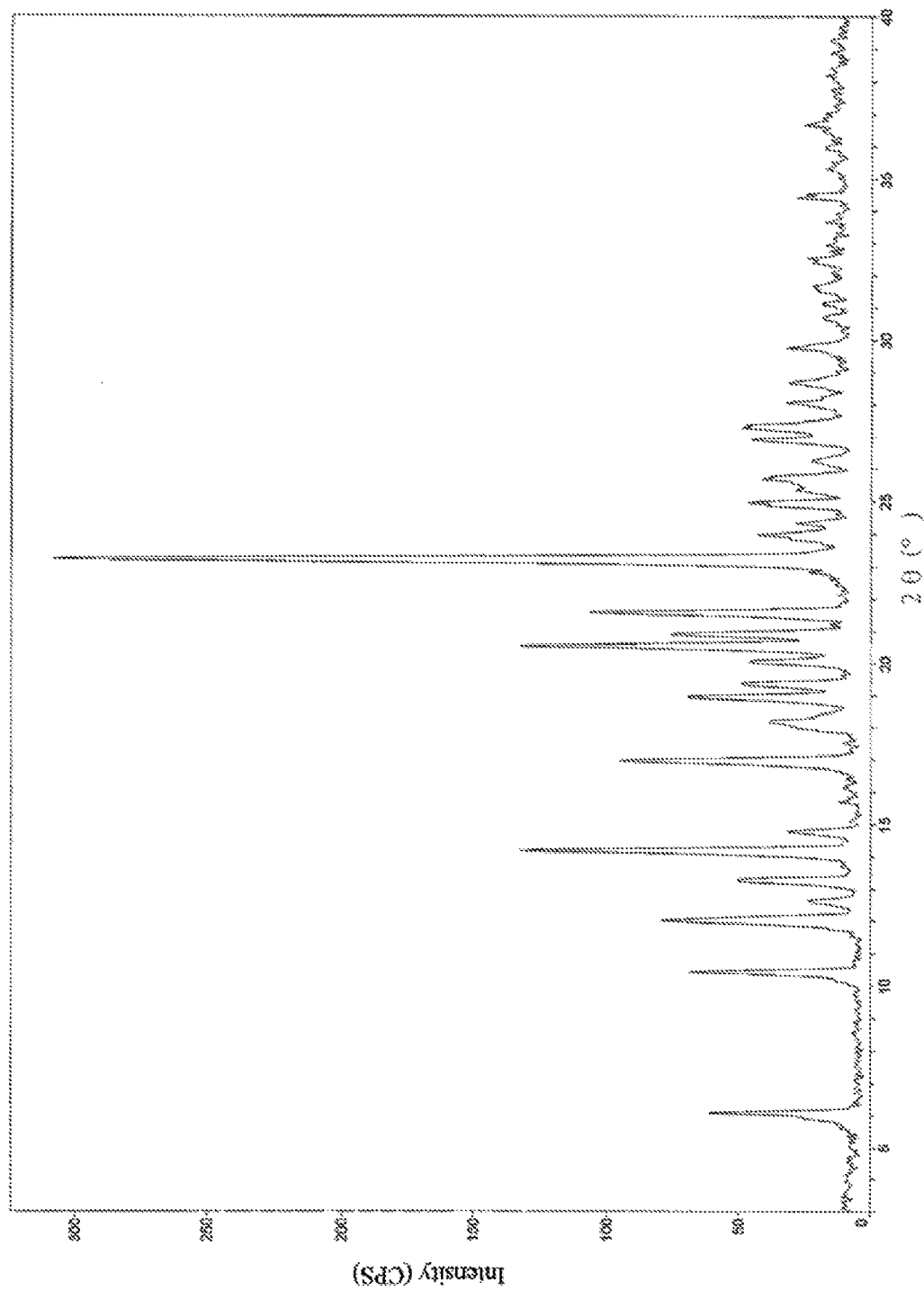
FIG. 11 is an X-ray powder diffraction pattern of crystal form III of bedaquiline fumarate obtained in Example 12.
Figure 12:
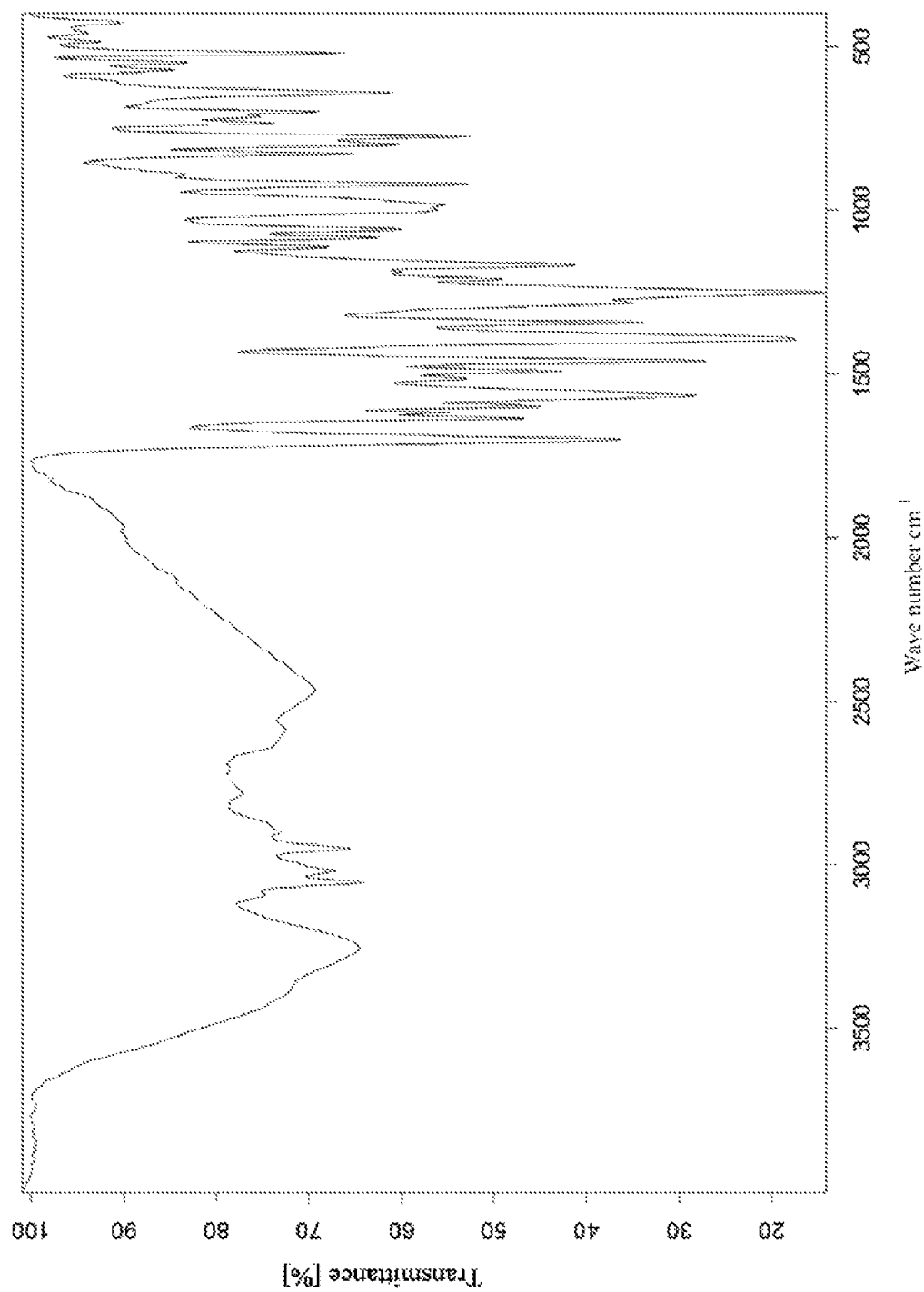
FIG. 12 is an infrared absorption spectrum of crystal form III of bedaquiline fumarate obtained in Example 12.
Figure 13:
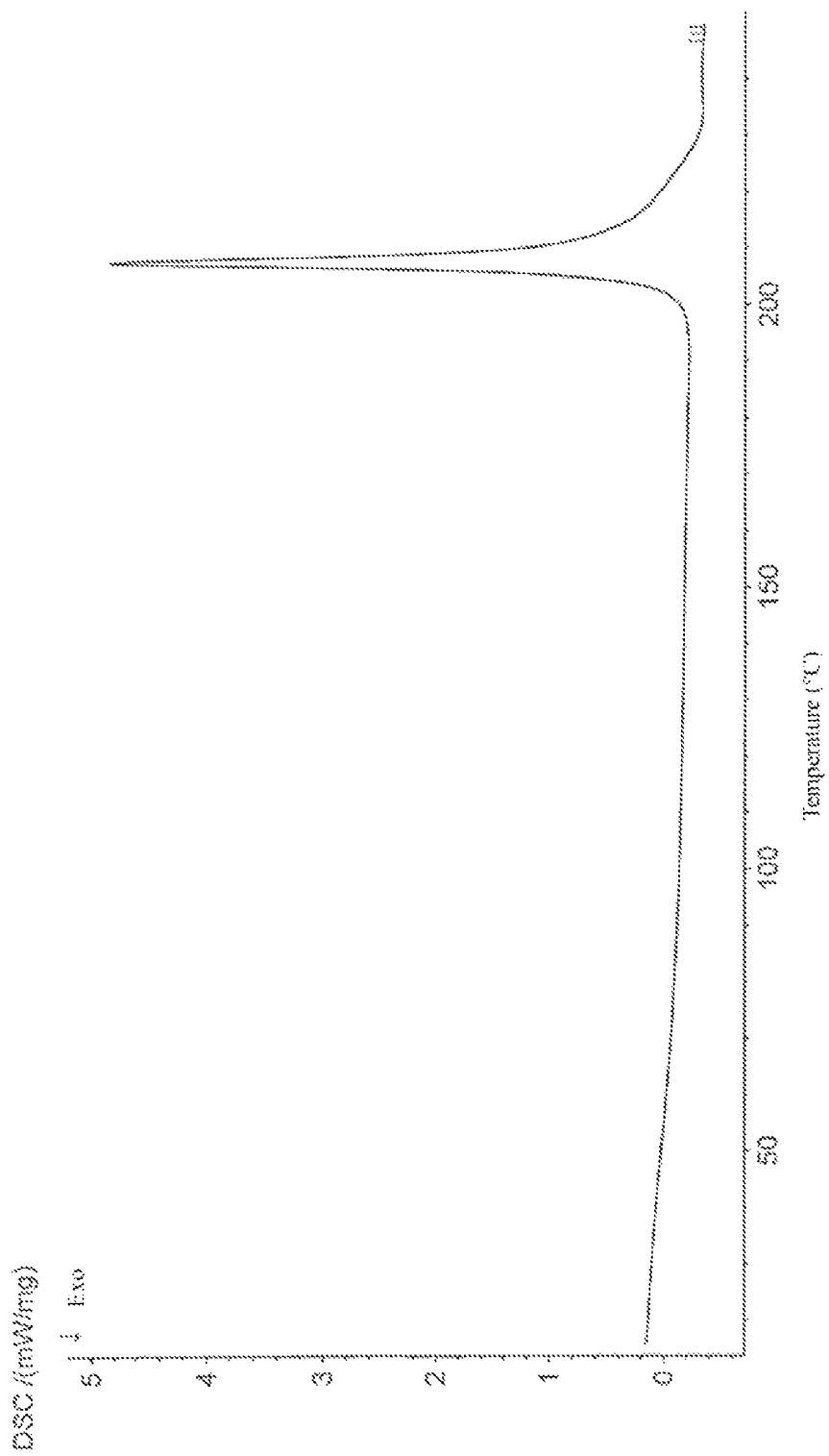
FIG. 13 is a DSC thermogram of crystal form III of bedaquiline fumarate obtained in Example 12.
Figure 14:
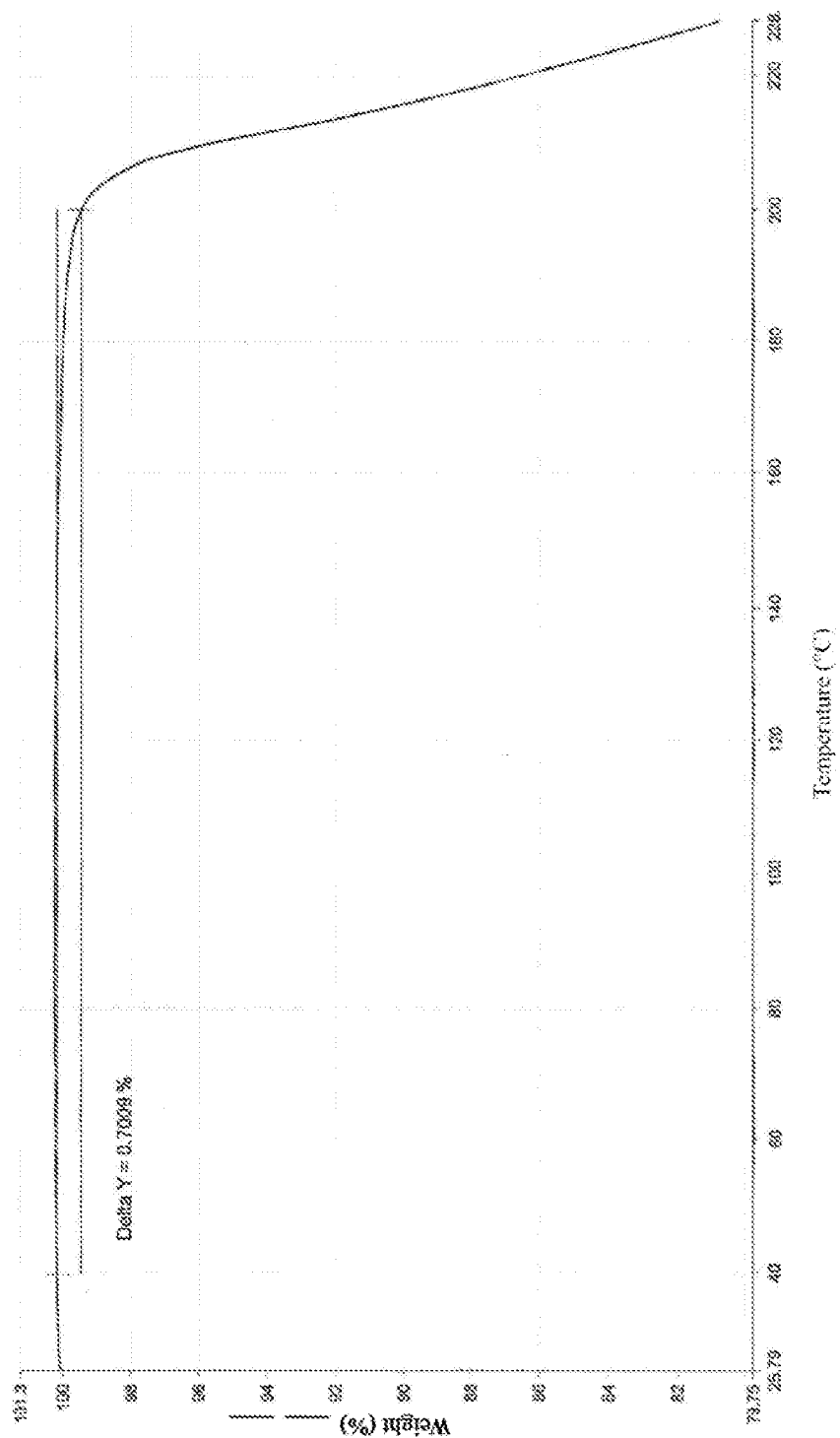
FIG. 14 is a TGA thermogram of crystal form III of bedaquiline fumarate obtained in Example 12.

X-ray powder diffraction, infrared, DSC, and TGA measurements confirmed that the product was the crystal form III of bedaquiline fumarate, the X-ray powder diffraction pattern, infrared absorption spectrum, DSC thermogram and TGA thermogram are shown in FIGS. 11-14, respectively.

Example 13

1 g of bedaquiline fumarate crude product (HPLC purity >99%) was dissolved in 80 ml of isopropanol, the solution was heated up to 60° C. and was stirred continuously for 30 min to dissolve; filtered, the stirring rate was controlled at 200 rpm/min, the filtrate was cooled to 0° C. at a rate of 6° C./h, and was crystallized under stirring at 0° C. for 4 h, filtered, dried under vacuum at 40° C. to give 0.45 g of crystals, HPLC=99.7%.

X-ray powder diffraction, infrared, DSC, and TGA measurements confirmed that the product was the crystal form III of bedaquiline fumarate.

Example 14

1 g of bedaquiline fumarate crude product (HPLC purity >99%) was dissolved in 60 ml of isopropanol, the solution was heated up to 80° C. and was stirred continuously for 30 min to dissolve; filtered, the stirring rate was controlled at 200 rpm/min, the filtrate was cooled to 0° C. at a rate of 6° C./h, and was crystallized under stirring at 0° C. for 4 h, filtered, dried under vacuum at 40° C. to give 0.51 g of crystals, HPLC=99.7%.

X-ray powder diffraction, infrared, DSC, and TGA measurements confirmed that the product was the crystal form III of bedaquiline fumarate.

Example 15

1 g of bedaquiline fumarate crude product (HPLC purity >99%) was dissolved in 70 ml of isopropanol, the solution was heated up to 80° C. and was stirred continuously for 30 min to dissolve; filtered, the stirring rate was controlled at 200 rpm/min, the filtrate was cooled to 3° C. at a rate of 6° C./h, and was crystallized under stirring at 3° C. for 4 h, filtered, dried under vacuum at 40° C. to give 0.50 g of crystals, HPLC=99.7%.

X-ray powder diffraction, infrared, DSC, and TGA measurements confirmed that the product was the crystal form III of bedaquiline fumarate.

Example 16

The crystal form I, crystal form II and crystal form III of bedaquiline fumarate prepared respectively in Example 1, Example 6 and Example 12 of the present invention were selected for test of particle size.

Preparation of suspension of samples: the samples of the crystal form I, crystal form II and crystal form III of bedaquiline fumarate above (each 20 mg) were taken, about 5.0 ml n-hexane (dispersant) was added, the samples were subjected to ultrasonication for 1.0 min, were allowed to stabilize for 0.5-1.0 min then were tested.

Test Procedure: the Hydro2000SM injector was connected and the Small Volume Sample Dispersion Unit tachometer was turned on, then a suitable amount of ethanol was added to the sample cell to clean the detection channel of the instrument. A suitable amount of n-hexane (dispersant) was added to the dispersion cup, a suitable amount of n-hexane (dispersant) was inlet into the instrument to exhaust gas, the stirring rate was set to 2950 rpm, optical correction and background measurement were carried out.

The suspension was added to the sample cell until the opacity was between 15% to 20%, the suspension was allowed to stabilize for 0.5-1.0 min, the measurement time was 4 sec, the test results was saved automatically by the system.

The test results are shown in Table 5.

TABLE 5

|  | D (0.1) | D (0.5) | D (0.9) |
|---|---|---|---|
| Crystal form I non-micronized | 4.991 um | 16.303 um | 37.967 um |
| Crystal form II non-micronized | 3.146 um | 12.646 um | 37.019 um |
| Crystal form III non-micronized | 10.034 um | 33.721 um | 68.295 um |

The test results show that the particle sizes of the crystal form I and crystal form II of bedaquiline fumarate were smaller than that of the crystal form III. The smaller the particle size, the bigger the specific surface area, and bigger specific surface area was conducive to improving the dissolution behavior, and the improved dissolution behavior was considered to improve the bioavailability. In addition, according to the actual test results, it was found that the particles of the three crystal forms were dispersed homogeneously, in the actual production, a step of micronization or screening process was reduced and costs were saved.

Table 6 shows the solubility data of the different crystal forms prepared in the present invention in different solvents at 50° C.

The crystal form I, the crystal form II and the crystal form III of bedaquiline fumarate prepared respectively in Example 1, Example 6 and Example 12 of the present invention were selected for solubility test.

TABLE 6

| Solvent | Crystal form I (g/ml) | Crystal form II (g/ml) | Crystal form III (g/ml) |
|---|---|---|---|
| Methanol | 2 | 6 | 6 |
| Ethanol | 25 | 20 | 22 |
| Isopropanol | 60 | 100 | 70 |
| Acetonitrile | 120 | 80 | 90 |
| Ethyl acetate | 60 | 60 | 60 |
| Tetrahydrofuran | 1 | 5 | 3 |
| Acetone | 4 | 30 | 25 |
| N,N-dimethylformamide | 1 | 2 | 3 |
| Water | insoluble | insoluble | insoluble |

Table 7 shows the test results of stability by liquid chromatography of the different crystal forms prepared according to the present invention at a temperature of 60° C. and a humidity of 75% for 6 months.

The crystal form I, the crystal form II and the crystal form III of bedaquiline fumarate prepared respectively in Example 1, Example 6 and Example 12 of the present invention were selected for liquid chromatography test.

TABLE 7

|  | 0 month | 1 month | 2 months | 3 months | 6 months |
|---|---|---|---|---|---|
| Crystal form I | 99.7% | 99.6% | 99.6% | 99.6% | 99.5% |
| Crystal form II | 99.7% | 99.7% | 99.7% | 99.6% | 99.5% |
| Crystal form III | 99.6% | 99.6% | 99.5% | 99.5% | 99.4% |

Six months later, the crystal form I, the crystal form II and the crystal form III of bedaquiline fumarate were all very stable. Stable means degradation was not found and transition to other crystal forms was not detected by liquid chromatography, infrared, and XRPD analysis.

The invention claimed is:

1. A crystal form I of (1R,2S)-1-(6-bromo-2-methoxyquinolin-3-yl)-4-dimethylamino-1-phenyl-2-(1-naphthyl)-2-butanol fumarate, wherein the X-ray powder diffraction pattern thereof has characteristic peaks at 2θ (°) values of 5.6±0.2, 11.2±0.2, 22.6±0.2, 23.1±0.2, 23.6±0.2, 29.0±0.2.

2. The crystal form I according to claim 1, wherein the X-ray powder diffraction pattern thereof has additional characteristic peaks at 2θ (°) values of 3.8±0.2, 16.9±0.2, 18.8±0.2, 19.3±0.2, 20.6±0.2, 20.9±0.2, 21.9±0.2, 26.7±0.2, 28.3±0.2.

3. A preparation method of crystal form I of (1R,2S)-1-(6-bromo-2-methoxyquinolin-3-yl)-4-dimethylamino-1-phenyl-2-(1-naphthyl)-2-butanol fumarate according to claim 1, wherein the method comprises the following sequence of steps:
(1) (1R,2S)-1-(6-bromo-2-methoxyquinolin-3-yl)-4-dimethylamino-1-phenyl-2-(1-naphthyl)-2-butanol fumarate is dissolved in a mixed solvent of methanol and water;
(2) the temperature is increased to 50-60° C. and the solution is stirred continuously until the solute dissolved;
(3) filtered, the filtrate is stirred to decrease the temperature to 10-25° C.; and
(4) crystallized at 10-25° C., filtered to obtain the crystal form I of (1R,2S)-1-(6-bromo-2-methoxyquinolin-3-yl)-4-dimethylamino-1-phenyl-2-(1-naphthyl)-2-butanol fumarate.

4. The preparation method according to claim 3, wherein the weight-to-volume ratio of (1R,2S)-1-(6-bromo-2-methoxyquinolin-3-yl)-4-dimethylamino-1-phenyl-2-(1-naphthyl)-2-butanol fumarate to the mixed solvent of methanol and water is 1:10-50 g/ml, preferably 1:10-20 g/ml; the volume percentage of water is 10%-70%, preferably 20%-40%.

* * * * *